United States Patent [19]

Djedaini-Pilard et al.

[11] Patent Number: 5,760,017

[45] Date of Patent: Jun. 2, 1998

[54] CYCLODEXTRIN DERIVATIVES USABLE IN PARTICULAR FOR SOLUBILIZING HYDROPHOBIC CHEMICAL COMPOUNDS SUCH AS MEDICAMENTS AND THEIR PREPARATION PROCESS

[75] Inventors: Florence Djedaini-Pilard, Etampes; Nathalie Azaroual-Bellanger, Wattignies; Bruno Perly, La Verriere, all of France

[73] Assignee: Commissariat a l'Energie Atomique, Paris, France

[21] Appl. No.: 652,470

[22] PCT Filed: Dec. 21, 1994

[86] PCT No.: PCT/FR94/01501

§ 371 Date: Dec. 5, 1996

§ 102(e) Date: Dec. 5, 1996

[87] PCT Pub. No.: WO95/17432

PCT Pub. Date: Jun. 29, 1995

[30] Foreign Application Priority Data

Dec. 22, 1993 [FR] France ................... 93 15472

[51] Int. Cl.⁶ .......................... A01K 31/70; C08B 30/18
[52] U.S. Cl. ........................ 514/58; 536/46; 536/103
[58] Field of Search ................ 514/58; 536/55.1, 536/46, 103

[56] References Cited

FOREIGN PATENT DOCUMENTS 9113100  9/1991  WIPO .

OTHER PUBLICATIONS

Chemistry Letters vol. 10,1976, JP pp. 1037–1040 Y. Matsui et al. 'Catalytic properties of a Cu (II) complex with a modified cyclodetrin' p. 1037, ligne 15— p. 1038, ligne 2.

*Primary Examiner*—Elli Peselev
*Attorney, Agent, or Firm*—Oblon, Spivak, McClelland, Maier & Neustadt, P.C.

[57] ABSTRACT

The invention relates to novel cyclodextrin derivatives according to formula:

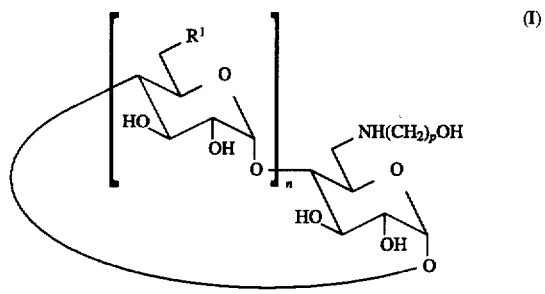

in which $R^1$ represents OH or $NH(CH_2)_pOH$, n is equal to 5, 6 or 7 and p is an integer from 2 to 6, it being possible for the p to be different when one or more of the $R^1$ represent $NH(CH_2)_pOH$.

These derivatives can be used for solubilizing hydrophobic chemical compounds such as active principles in an aqueous medium by the formation of inclusion complexes therewith.

18 Claims, No Drawings

CYCLODEXTRIN DERIVATIVES USABLE IN PARTICULAR FOR SOLUBILIZING HYDROPHOBIC CHEMICAL COMPOUNDS SUCH AS MEDICAMENTS AND THEIR PREPARATION PROCESS

The present invention relates to novel cyclodextrin derivatives more particularly usable for solubilizing in an aqueous medium hydrophobic chemical compounds, such as pharmaceutically active molecules, by inclusion in said derivatives.

Cyclodextrins or cyclomaltooligosaccharides are compounds having a natural origin forming by a linking of 6, 7 or 8 glucose units bonded in α1,4. Numerous works have shown that these cyclodextrins could form inclusion complexes with hydrophobic molecules and thus permit the solubilization of these molecules in aqueous media. Numerous applications have been proposed for taking advantage of this phenomenon, particularly in the pharmaceutical field, as is described by D. Duchêne in the work entitled "Cyclodextrins and their industrial uses", chapter 6, pp 213 to 257, Editions de Santé, 1987. Pharmaceutical compositions using these cyclodextrins have also been marketed in Japan and Italy and more recently in France, e.g. by Pierre Fabre Médicament for Brexin®, which is an inclusion complex of Piroxicam in β-cyclodextrin.

Among the usable cyclodextrins, β-cyclodextrin, which has 7 glucose units, is the most appropriate with regards to the size of its cavity and is the least expensive of the three, but its use causes certain problems, because it is less soluble than other cyclodextrins and has a hemolytic character.

Consideration has also been given to the improvement of the properties of β-cyclodextrin by chemically modifying to make it more suitable. Several solutions have been envisaged and have led to the use of methyl derivatives or hydroxyalkyl derivatives.

Methyl derivatives are much more soluble than the original cyclodextrin and they have good properties of solubilizing hydrophobic, organic compounds, particularly in the case of 2,6-dimethyl-β-cyclodextrin. However, these methyl derivatives, apart from the fact that they are difficult to obtain in the pure state, are unusable for pharmaceutical applications, particularly for injection forms, due to their very pronounced hemolytic character.

The hydroxyalkyl derivatives more particularly developed by Janssen, e.g. hydroxypropyl-cyclodextrins have a very high solubility in water and are only slightly hemolytic. However, their use remains difficult due to their extreme chemical heterogeneity. In addition, substitutions can limit the formation of inclusion complexes by steric hindrance and as yet no pharmaceutical application has been developed with these derivatives.

More recently consideration has been given to the use of other cyclodextrin derivatives, as is described in WO-A-91/13100. Among these derivatives there are those substituted by a diamine, but the results obtained with these diamino derivatives are not entirely satisfactory for pharmaceutical applications.

The present invention specifically relates to novel cyclodextrin derivatives usable for solubilizing hydrophobic chemical compounds and which obviate these disadvantages.

These novel cyclodextrin derivatives comply with the formula:

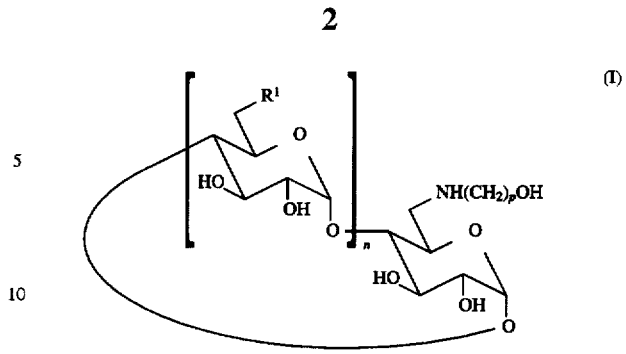

in which $R^1$ represent OH or $NH(CH_2)_pOH$, n is equal to 5, 6 or 7 and p is an integer from 2 to 6, in which the p can differ when one or more of the $R^1$ represent $NH(CH_2)_pOH$.

According to a first embodiment of the invention, the cyclodextrin derivative is a monosubstituted derivative, i.e. in the aforementioned formula I, all the $R^1$ represent OH.

Such a derivative can be prepared by reacting a tosyl derivative of formula:

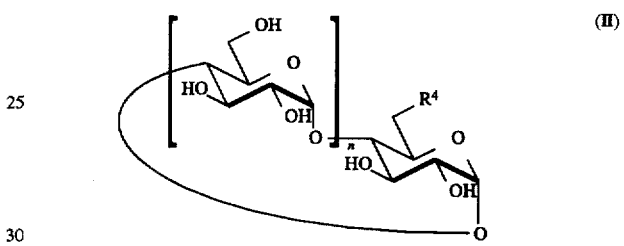

in which $R^4$ represents the tosyl group and n is equal to 5, 6 or 7 with a compound of formula $NH_2(CH_2)_pOH$ with p having the meaning given hereinbefore.

The tosyl derivative of formula (II) can e.g. be obtained by the process described in J. Am. Chem. Soc., 112, 1990, pp 3860–3868.

The reaction of the tosyl derivative with the compound of formula $NH_2(CH_2)_pOH$ can be simply carried out by dissolving the tosyl derivative in said compound.

According to a second embodiment of the invention, the cyclodextrin derivative is a per-substituted derivative, i.e. complying with formula I, in which all the $R^1$ represent a $NH(CH_2)_pOH$ group with p having the meaning given hereinbefore.

These per-substituted derivatives are particularly interesting, because the presence of several $NH (CH_2)_pOH$ groups makes it possible to greatly increase their solubility in water.

These derivatives can be prepared from periodo derivatives of cyclodextrins by reacting an iodocyclodextrin derivative complying with the formula:

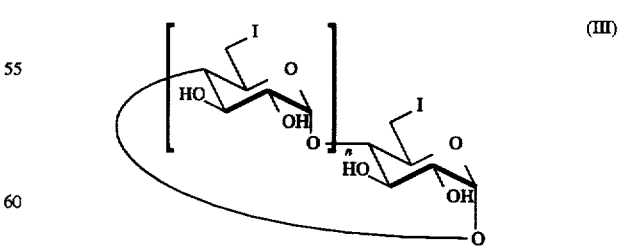

in which n is equal to 5, 6 or 7, with at least one compound of formula $NH_2(CH_2)_pOH$ in which p has the meaning given hereinbefore.

Preferably, in the second embodiment of the invention, all the $R^1$ of the derivative of formula (I) are identical. In this case, use is made of a single compound of formula NH$_2$(CH$_2$)$_p$OH for obtaining the per-substituted derivative.

The cyclodextrin derivatives described hereinbefore are more particularly usable for the solubilization in the aqueous medium of hydrophobic chemical compounds.

The invention also relates to a process for solubilizing in an aqueous medium a hydrophobic chemical compound consisting of combining this compound with a cyclodextrin derivative according to formula (I), for forming therewith a water-soluble inclusion complex.

The use in this process of derivatives complying with formula (I) has the advantage of improving the solubility, stability and bioavailability, in various administration forms of the hydrophobic compound, particularly in the case of pharmaceutically active molecules.

Preferably, according to the invention, use is made of mono or per-substituted derivatives of β-cyclodextrin, i.e. in formula I n is equal to 6. However, it is also possible to use derivatives of α-cyclodextrin (n=5) and derivatives of γ-cyclodextrin (n=7).

The hydrophobic chemical compounds which can be solubilized in aqueous media by means of these cyclodextrins can be of different types.

Examples of such compounds are cosmetic products, vitamins and pharmaceutically active molecules such as those described by D. Duchêne in the work entitled "Cyclodextrins and their industrial uses", chapter 6, pp 213 to 257, Editions de Santé, 1987.

Preferably, in the invention, the hydrophobic chemical compound is a pharmaceutically active molecule.

Examples of such molecules are steroids, e.g. prednisolone, anti-epileptic agents such as carbamazepine, and anti-cancer agents.

The invention also relates to inclusion complexes of the cyclodextrin derivatives referred to hereinbefore with a chemical and in particular hydrophobic compound, such as a pharmaceutically active molecule.

These inclusion complexes can be prepared by conventional processes, e.g. by adding to a solution or a suspension of the cyclodextrin derivative of formula (I), a solution of the compound in an appropriate organic solvent, e.g. acetone. It is also possible to isolate the thus formed inclusion complex by lyophilization. The invention also relates to a pharmaceutical composition incorporating an inclusion complex of a cyclodextrin derivative of formula (I) and a pharmaceutically active molecule, with a pharmaceutically acceptable vehicle.

These pharmaceutical compositions, which can be orally or parenterally administered, are e.g. solutions, powders, suspensions, etc., more particularly injectable solutions.

Other features and advantages of the invention can be better gathered from the following non-limitative, illustrative examples.

EXAMPLE 1

Preparation of mono-6-ethanolamino-6-deoxycyclomaltoheptaose

This derivative is the monosubstituted derivative of formula I with all the R$^1$ representing OH, R$^2$ representing OH, p being equal to 2 and n equal to 6.

Firstly the tosyl derivative of formula II is prepared with n=6 and operating in the following way. 60 g of cyclomaltoheptaose (52.8 mmole) are suspended in 500 ml of distilled water. Dropwise addition takes place of 6.57 g (164 mmole) of caustic soda dissolved in 20 ml of water for 5 minutes and with strong magnetic stirring. To the clear solution obtained are added 10.08 g (52.9 mmole) of p-toluene sulphonyl chloride (tosyl chloride) in 30 ml of acetonitrile in dropwise manner for 10 minutes. After stirring for 2 hours at ambient temperature, the precipitate formed is eliminated by filtration and the filtrate is kept for 48 hours at 4° C. The precipitate is isolated by filtration in vacuo, washed with 50 ml of ice water and immediately recrystallized in boiling water. After one night at 4° C., the precipitate is filtered and dried in vacuo at 30° C. This gives 7.5 g (12%) of a pure compound in accordance with the specifications.

In a flask 2 g (1.55 mmole) of 6-tosyl-6-deoxycyclomaltoheptaose obtained previously after dissolved in 8 ml of pure ethanol amine. Stirring of the reaction mixture is maintained for 3 days at ambient temperature, followed by the dropwise addition of the reaction mixture to 200 ml of absolute ethanol. The suspension is kept at 0° C. for 3 days, followed by the filtration of the precipitate in vacuo and its washing with absolute ethanol and then acetone. The solid obtained is redissolved in water and lyophilized. This gives 1.1 g of 6-ethanolamino-6-doxycyclomaltoheptaose, which corresponds to a 60% yield.

This compound has the following characteristics:

Thin layer chromatography (Merck silica plates) Rf=0.60 in a mixture of 6% NH$_4$OH/ethanol/n-butanol 5:5:1 (v:v), revealing by 10% H$_2$SO$_4$.

Mass spectrometry: electrospray method: m/z=1178[M+H]$^+$

NMR (500 MHz, 10 mmole/l solution in heavy water) H-1:5.12 ppm, H-6a and H-6a':2.891 and 3.15 ppm NH-CH$_2$:2.8 ppm, H-4a:3.50 ppm, CH$_2$OH:3.64 ppm other protons of the cyclodextrin: 3.6 to 3.8 and 3.85 to 4.05 ppm.

Elementary analysis C$_{44}$H$_{75}$NO$_{35}$, 3H$_2$O:

|  | C | H | N | O |
|---|---|---|---|---|
| Calculated | 42.89 | 6.63 | 1.14 | 49.34 |
| Found | 41.7 | 6.55 | 1.18 | 48.6 |

Solubility in water under physiological conditions (sodium phosphate buffer, pH 7.40, 25° C.): 40 mmole/l in free base form and 95 mmole/l in hydrochloride form.

EXAMPLE 2

Preparation of heptakis-6-ethanolamino-6-deoxycyclomaltoheptaose

This derivative is the derivative of formula I in which all the R$^1$ represent NH—CH$_2$—CH$_2$—OH, R$^2$ representing OH, p is equal to 2 and n is equal to 6.

In 6 ml of ethanol amine are dissolved 300 mg (0.157 mmole) of heptakis (6-iodo-6-deoxy)-cyclomaltoheptaose and stirring of the reaction mixture is maintained under an argon atmosphere and at ambient temperature for 18 hours. After concentration in vacuo to approximately 1 ml, the solution is poured dropwise and accompanied by vigorous stirring into 200 ml of anhydrous acetone. The precipitate obtained is isolated by filtration, washed with acetone and then dried in vacuo at 30° C. The residue is redissolved in 2 ml of water, followed by filtration on Millex GS (0.2 µm) and lyophilization. This gives 0.177 g of heptakis-6-ethanolamino-6-deoxy-cyclomaltoheptaose, which corresponds to a 78% yield.

This compound has the following characteristics:

Thin layer chromatography on Merck silica gel: Rf 0.65 in the 6% NH$_4$OH/ethanol/n-butanol mixture.

NMR (20 mmole/l solution in water): the spectra both in the proton and C13 indicate a complete symmetry of the molecule and therefore a per-substitution.

NMR of the proton. Allocation by homonuclear correlation to two quanta (500 MHz, 298K) 5.153 (H-1), 3.68 (H-2), 4.0 (H-3), 3.55 (H-4), 3.99 (H-5), 2.92 and 3.05 (H-6$_{ab}$), 2.8 (NH—CH$_2$—CH$_2$—OH), 3.71 and 3.74 (NH—CH$_2$—CH$_2$—OH). NMR of carbon 13, allocation by bidimensional C-H correlation: 102.6 (C-1), 73.5 (C-2), 74.0 (C-3), 83.9 (C-4), 71.5 (C-5), 50.3 (C-6), 51.7 (NH—CH$_2$—CH$_2$—OH), 61.1 (NH—CH$_2$—CH$_2$—OH).

Solubility in water under physiological conditions (sodium phosphate buffer, pH 7.40, 25° C.): 140 mmole/l in free base form and 350 mmole/l in hydrochloride form.

EXAMPLE 3

Preparation of a complex of heptakis-6-ethanolamino-6-deoxycyclomaltoheptaose and prednisolone The prednisolone is in accordance with the following formula:

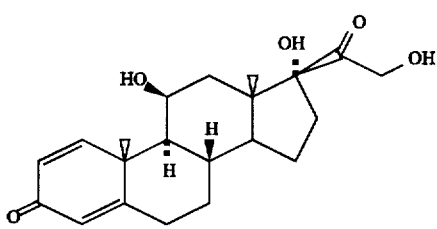

and has a very low solubility in water (0.25 mg/ml at 25° C., i.e. 0.7 mmole/l).

10 µmole of heptakis-6-ethanolamino-6-deoxycyclomaltoheptaose (in hydrochloride form) prepared in example 1, are dissolved in 1 ml of pure water (apyrogenic water for injection) and addition takes place of 5 µmole of prednisolone in the form of a 50 mmole/l concentrated solution in acetone. The acetone is eliminated by nitrogen passage for 10 minutes and the solution is lyophilized.

The residual solid, which contains 10 µmole of the cyclodextrin derivative and 5 µmole of prednisolone, is redissolved in the minimum of water at 25° C. This minimum corresponds to 160 µl of water, which indicates a 30 mmole/l solubility of prednisolone in water, in the presence of said cyclodextrin derivative at a concentration of 60 mmole/l.

Under the same conditions, the maximum prednisolone solubility reached in the case of the monosubstituted derivative of example 1 is 18 mmole/l. Under the same conditions, β-cyclodextrin only makes it possible to solubilize the prednisolone at 9 mmole/l.

Thus, the per-substituted derivative of β-cyclodextrin according to the invention makes it possible to achieve a much better result.

For comparison purposes and under the same conditions as those of examples 1, 2 and 3, the β-cyclodextrin derivative according to WO-A-91/13100 according to the above formula (I), in which all the R$^1$ represent OH, n is equal to 6 and NH(CH$_2$)$_p$OH is replaced by NH—CH$_2$—CH$_2$—NH$_2$, has a maximum solubility in water of 70 mmole/l and only makes it possible to solubilize the prednisolone at 12 mmole/l.

Thus, the derivatives according to the invention are of great interest, because they are much more soluble in water than β-cyclodextrin, whose solubility in water is 15 mole/l (18 g/l) at 25° C., whereas the hydrochloride of the per-substituted derivative has a solubility of 350 mmole/l.

Therefore they have a high solubilizing power for numerous active principles. In addition, they have a very weak hemolytic character.

Thus, the hemolytic properties of the derivative obtained in example 1 were tested by contacting 0.4 ml of a solution of human erythrocytes and 4 ml of the 5 mmole/l hydrochloride solution, at a pH of 7.4, for 30 minutes and 37° C. Under these conditions no hemolysis was observed, whereas the hemolysis level is 50% with β-cyclodextrin under the same conditions.

Moreover, ionization potential measurements (pK) carried out by potentiometry revealed that these derivatives are in the optimum buffer power zone for physiological conditions, which makes them interesting for parenteral applications.

Thus, the monosubstituted derivative of example 1 has a single pK at 7.10. The per-substituted derivative of example 2 has a single pK at 7.05.

Thus, under physiological conditions (pH approximately 7.2 to 7.4), these derivatives are in the optimum buffer power zone (the buffer power is optimum around the pK value).

However, in the case of the derivative of formula (I) in accordance with WO-A-91/13100 with R$^1$=OH, n=6 and NH(CH$_2$)$_p$OH replaced by NH—CH$_2$—CH$_2$—NH$_2$, there are two pK's at 7.5 and 9.5.

Finally, the derivatives according to the invention are easy to obtain, in the form of single chemical species, which are perfectly characterized and without it being necessary to use complex purification stages.

We claim:

1. A cyclodextrin having the formula:

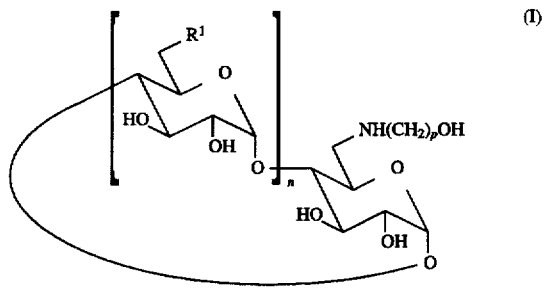

in which each R$^1$ is OH or NH(CH$_2$)$_p$OH, n is 5, 6 or 7, p is an integer from 2 to 6, and each p may be different when one or more of R$^1$ is NH(CH$_2$)$_p$OH.

2. The cyclodextrin according to claim 1, wherein all R$^1$ are OH.

3. The cyclodextrin according to claim 1, wherein all R$^1$ are NH(CH$_2$)$_p$OH.

4. The cyclodextrin according to claim 1, wherein all p are identical.

5. The cyclodextrin according to claim 1, wherein p is 2.

6. The cyclodextrin according to claim 1, wherein n is 6.

7. The cyclodextrin according to claim 2, wherein n is 6.

8. The cyclodextrin according to claim 3, wherein n is 6.

9. The cyclodextrin according to claim 4, wherein n is 6.

10. The cyclodextrin according to claim 5, wherein n is 6.

11. A process for the preparation of the cyclodextrin according to claim 2, comprising reacting a cyclodextrin of formula:

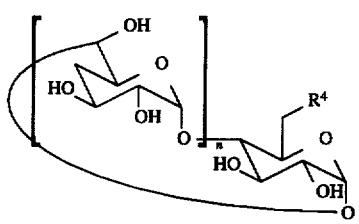

(II)

in which $R^4$ is a tosyl group, and n is 5, 6 or 7, with at least one compound of formula $NH_2(CH_2)_pOH$ wherein p is an integer from 2 to 6.

12. A process for the preparation of a cyclodextrin according to claim 3, comprising reacting an iodocyclodextrin of formula:

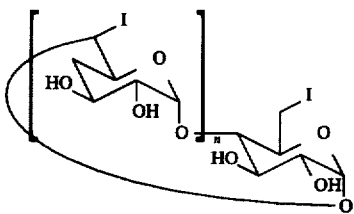

(III)

in which n is 5, 6 or 7, with at least one compound of formula $NH_2(CH_2)_pOH$ in which p is an integer of 2–6.

13. A process for solubilizing in an aqueous medium a hydrophobic chemical compound, comprising mixing said hydrophobic chemical compound with the cyclodextrin according to claim 1 to form a water-soluble inclusion complex.

14. The process according to claim 13, wherein said hydrophobic compound is a pharmaceutically active molecule.

15. An inclusion complex of the cyclodextrin according to claim 1 and a hydrophobic chemical compound.

16. The complex according to claim 15, wherein said chemical compound is a pharmaceutically active molecule.

17. The complex according to claim 16, wherein said pharmaceutically active molecule is prednisolone.

18. A pharmaceutical composition, comprising the inclusion complex of claim 16, and a pharmaceutically acceptable vehicle.

* * * * *